US007468172B2

(12) United States Patent  (10) Patent No.: US 7,468,172 B2
Godber et al. (45) Date of Patent: Dec. 23, 2008

(54) HYDROXAPATITE CALCIUM PHOSPHATES, THEIR METHODS OF PREPARATION AND THEIR APPLICATIONS

(75) Inventors: John Godber, Lawrenceville, NJ (US); Lorraine Leite, Brussels (BE)

(73) Assignee: Innophos, Inc., Cranbury, NJ (US)

( * ) Notice: Subject to any disclaimer, the term of this patent is extended or adjusted under 35 U.S.C. 154(b) by 217 days.

(21) Appl. No.: 11/125,690

(22) Filed: May 6, 2005

(65) Prior Publication Data

US 2005/0271571 A1 Dec. 8, 2005

(51) Int. Cl.
C01B 25/32 (2006.01)
A61K 9/16 (2006.01)
(52) U.S. Cl. .................................... 423/308; 424/489
(58) Field of Classification Search ................. 423/308, 423/309, 311
See application file for complete search history.

(56) References Cited

U.S. PATENT DOCUMENTS

| | | | | |
|---|---|---|---|---|
| 4,355,086 | A | | 10/1982 | Saathoff et al. |
| 4,891,198 | A | * | 1/1990 | Ackilli et al. ................ 423/308 |
| 6,117,456 | A | * | 9/2000 | Lee et al. ..................... 424/602 |
| 6,582,672 | B1 | * | 6/2003 | Bonfield et al. ............. 423/308 |
| 6,585,946 | B1 | * | 7/2003 | Bonfield et al. ............. 423/308 |

FOREIGN PATENT DOCUMENTS

| | | |
|---|---|---|
| FR | 2 799 193 | 10/1999 |
| FR | 2 857 658 | 7/2003 |
| FR | 2 852 243 | 3/2004 |
| WO | WO 99/32400 | 7/1999 |

OTHER PUBLICATIONS

Legeros et al, "Transformation of calcium carbonates and calcium phosphates to carbonate apatites: possible mechanism for phosphotite formation", Proceedings—International Congress on Phosphorus Compounds, 2nd, 41-57 (English) 1980. (Abstract only), no month.*
R. Z. Le Geros et al, "Transformation of Calcium Carbonates and Calcium Phosphates to Carbonate Apatites: Possible Mechanism for Phosphorite Formation", Proceedings-International Congress on Phosphorus Compounds, 2 , 41-57 (English) 1980, no month.*

(Continued)

Primary Examiner—Wayne Langel
(74) Attorney, Agent, or Firm—McCarter & English, LLP

(57) ABSTRACT

The present invention is directed to calcium phosphates in granular form having an X-ray diffraction pattern characteristic of hydroxyapatite in which a portion of the anions of the crystal lattice are substituted with carbonate anions and which have good compressibility and flow properties in direct compression applications.

The invention is also directed to the methods for preparing the calcium phosphate aforesaid granules characterized in that the methods include the processing of a brushite dicalcium phosphate solution having a specified particle size distribution using a solution of an alkaline earth carbonate for a sufficient period of time to allow the transformation of the brushite calcium phosphate into hydroxyapatite calcium phosphate.

8 Claims, 2 Drawing Sheets

OTHER PUBLICATIONS

Biopharmaceutics. 2001, 51, 249-257, Abstract; p. 253, right column and table 1 and figures 3 and 4, no month.

International Search Report, Apr. 9, 2007.

Landi, E et al: "Carbonated Hydroxyapatite as Bone Substitute"; Journal of the European Ceramic Society, Elsevier Science Publishers, Barking, Essex, GB, vol. 23, No. 15, 2003, pp. 2931-2937, XP004450516 ISSN: 0955-2219, no month.

Patel N et al: "Preparation and Characterisation of Hydroxyapatite and Carbonate Substituted Hydroxyapatite Granules", Key Engineering Materials 2001 Trans Tech Publ, Uetikon-Zuerich, Switzerland, vol. 192-195, Nov. 22, 2000, pp. 7-10, XP008041149.

Database Compendex 'Online! Engineering Information, Inc., New York, NY, US; Monma Hideki; "Hydration and Hardening of Brushite and Monetite" XP002312637, Database accession No. EIX87060088346 & Yogyo Kyokai Shi 1987, vol. 95, No. 2 part 2, 1987, pp. 284-285, no month.

Monma H et al: "Preparation of Hydroxyapatite by the Hydrolysis of Brushite", Dec. 1987, Journal of Materials Science, Chapman and Hall Ltd. London, GB, pp. 4247-4250, XP001161107, ISSN: 0022-2461, no month.

Itoh H et al: "A New Porous Hydroxyapatite Ceramic Prepared by Cold Isostatic Pressing and Sintering Synthesized Flaky Powder", Dental Materials Journal, vol. 13, No. 1, 1994, pp. 25-35, XP008027708, ISSN: 0287-4547, no month.

Pontier C et al: "About the Use of Stoichiometric Hyroxyapatite in Compression—Incidence of Manufacturing Process on Compressibility" European Journal of Pharmaceutics and Biopharmaceutics, Elsevier Science Publishers B.V., Amsterdam, NL, vol. 51, No. 3, May 2001, pp. 249-257, XP004239486, ISSN: 0939-6411.

Databse WPI, Section Ch, Week 199716, Derwent Publications Ltd., London, GB; AN 1997-175473, XP002313187 & JP 09 040408 A (Taihei Kagaku Sangyo KK), Feb. 10, 1997.

Werner Rathje: "Zur Kenntnis der Phosphate I: Über Hydroxylapatit"; Bodenkunde U. Planzernahr, vol. 12, 1939, pp. 121-128, XP008041263, pp. 125 a 126, "Darstellung von Hydroxylapatit", no month.

French Search Report for FR 04 04900 dated Jan. 12, 2005.

\* cited by examiner

HYDROXAPATITE CALCIUM PHOSPHATES, THEIR METHODS OF PREPARATION AND THEIR APPLICATIONS

This application claims priority under 35 U.S.C. § 119 to French patent application no. 04 04900 May 6, 2004, the entire contents of which are hereby incorporated by reference.

FIELD OF THE INVENTION

In one aspect, the present invention is directed to calcium phosphates that have X-ray diffraction patterns characteristic of the mineral hydroxyapatite, and which can be used as excipients. More specifically, the invention is directed to calcium phosphates in granular form having an X-ray diffraction pattern characteristic of hydroxyapatite in which a portion of the anions of the crystal structure are substituted with carbonate anions, and having good compressibility and flow properties in direct compression applications.

In another aspect, the invention is directed to particularly economical methods for preparing the calcium phosphate granules. In yet another aspect, the invention is directed to the use of the calcium phosphate granules as excipients in tablets preferably obtained via direct compression.

BACKGROUND OF THE INVENTION

French patent application no. 03/08660 previously described a method for forming a type of calcium phosphate hydroxyapatite, namely a product in granular form having good flow and compressibility properties. Hydroxyapatite is a natural mineral structure, often associated with bones and teeth, with a particular crystal lattice. As used herein, the term "hydroxyapatite" refers essentially to calcium phosphates that produce an X-ray diffraction pattern characteristic of hydroxyapatite. Hydroxyapatite is often designated in the trade by the term "tricalcic phosphate." The ideal chemical formula of hydroxyapatite is $Ca_5(PO_4)_3(OH)$. It is, however, well known in the literature that the hydroxyapatite crystal lattice is extremely tolerant of anion and cation substitutions in the crystal network.

For example, the substitution of cations with elements such as magnesium, strontium, barium, sodium, lead and a large number of other atoms is well known. Anion substitution can take three different forms. First, a portion of the trivalent phosphate groups $(PO_4^{3-})$ can be replaced by $HPO_4^{2-}$. This results in a nonstoichiometric apatite structure. Second, the trivalent phosphate groups $(PO_4^{3-})$ can be replaced by other complex anions such as carbonates or vanadates. Third, the hydroxyl group (OH) can be partially or completely replaced by other anions such as fluoride or chloride.

Coupled substitution, in which an ion is replaced by another ion with a different charge and in which the neutrality of the charge is maintained by substitutions elsewhere in the crystal lattice with ions of different charges or by vacancies in the crystal lattice, is also well known. In all of these substitutions, the factor that remains common, and distinguishes the material as being a hydroxyapatite, is its characteristic X-ray diffraction pattern.

French patent application no. 03/08660 describes a method for producing hydroxyapatite calcium phosphate granules having compressibility properties that are superior to other calcium phosphates. The calcium phosphate granules described therein also have a physical form that allows them to resist attrition, which retain significant internal porosity, and as a result dissolve rapidly when used. The structure of the calcium phosphate hydroxyapatite composition is obtained by a particular manufacturing method described in French patent application no. 03/08660.

The method for preparing the aforesaid hydroxyapatite calcium phosphate in granular form described in French patent application no. 03/08660 is characterized in that it involves processing a brushite dicalcium phosphate solution having a particle size such that 90% of the brushite particles are smaller than 260 microns and 90% of the particles are larger than 10 microns, using a basic solution, keeping the pH at no less than 7.0 for a sufficient period of time to allow the transformation of the brushite calcium phosphate into hydroxyapatite calcium phosphate. The method converts the brushite according to the following general equation for alkaline hydrolysis of brushite into hydroxyapatite:

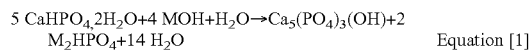

$$5\ CaHPO_4\cdot2H_2O + 4\ MOH + H_2O \rightarrow Ca_5(PO_4)_3(OH) + 2\ M_2HPO_4 + 14\ H_2O \qquad \text{Equation [1]}$$

in which M is the cation contributed by the base, preferably an alkaline cation, for example $Na^+$, $K^+$ or $NH_4^+$. The pH is kept at a value of not less than 7.0, preferably between 7 and 10 and more preferably between 8 and 8.5.

The method described in French patent application no. 03/08660 involves a hydroxide base. The use of the bases NaOH, $NH_4OH$, $Ca(OH)_2$ and KOH is recommended. The method produces a hydroxyapatite in granular form that can be represented by the following formula:

$$Ca_{5-x}(PO_4)_{3-x}(HPO_4)_x(OH)_{1-x} \qquad (i)$$

in which x varies between 0 and 1, and preferably between 0.1 and 0.5. As described in French patent application no. 03/08660, low quantities, for example less than 5% by weight, and preferably between 0.1 and 3% by weight, of calcium may be substituted with another cation, particularly the cation of the base (sodium, potassium). In addition, low quantities of trivalent phosphate groups $(PO_4^{3-})$ may be substituted with complex anions (for example carbonate and vanadate) and hydroxyl ions replaced with another anion, for example a halide, particularly chloride or fluoride.

As shown by Equation [1], along with the hydroxyapatite, large quantities of an alkali metal phosphate, $M_2HPO_4$, are produced in the reaction. Among the disadvantages of the method described in French patent application no. 03/08660 is that the alkali metal phosphate is difficult to recycle or upgrade. Also, depending upon the particular base used, undesirable impurities may be present in the calcium phosphate hydroxyapatite.

The present inventors have discovered a method to prepare calcium phosphate hydroxyapatite granules that have an X-ray diffraction pattern characteristic of the mineral hydroxyapatite that are completely suitable for use as an excipient and that avoid the disadvantages of the prior methods described above.

SUMMARY OF THE INVENTION

The present invention provides, in one aspect, calcium phosphate granules having X-ray diffraction patterns of hydroxyapatite. The calcium phosphate granules may have carbonate anions substituted for phosphate anions in the crystal lattice. The particle size of the calcium phosphate granules is generally such that the calcium phosphate granules have good flow properties and compressibility for use in a matrix to form tablets containing active ingredients for oral administration.

In a second aspect, the present invention provides methods of making calcium phosphate hydroxyapatite granules.

Brushite calcium phosphate is combined with a carbonate base, such as calcium carbonate, in a suspension in water. The suspension is preferably heated to a temperature greater than 50° C. for a sufficient period of time to allow the brushite and carbonate base to react to form the calcium phosphate hydroxyapatite having desirable flow and compressibility characteristics, and without production of undesirable by-products.

The calcium phosphate hydroxyapatite granules can be used in a matrix for combination with active ingredients to form tablets for oral administration.

BRIEF DESCRIPTION OF THE DESIGN

DESCRIPTION OF PREFERRED EMBODIMENTS

Figure 1:
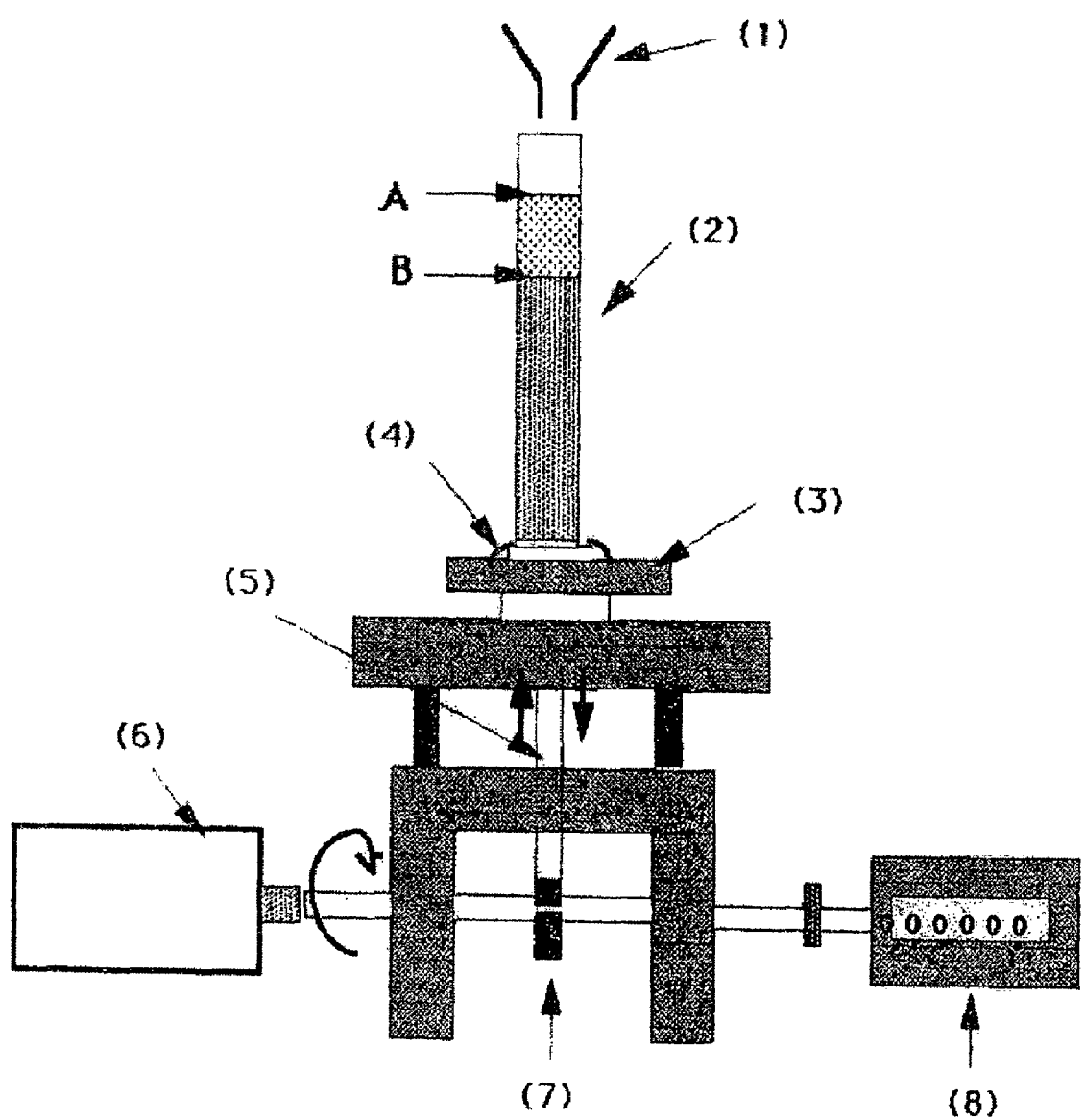
FIG. 1 illustrates an apparatus for measuring the apparent density, compacted and non-compacted, of the calcium phosphate hydroxyapatite granules.

The present invention relates to calcium phosphate hydroxyapatite granules having improved flow and compressibility characteristics which may be used as an excipient in, for example, pharmaceutical compositions or dietary supplements. The present invention also relates to methods of preparing the calcium phosphate hydroxyapatite granules to achieve the desired properties for the granules with reduced levels of undesirable impurities or secondary products.

The method for preparing the calcium phosphate hydroxyapatite in granular form is characterized by the processing of a brushite dicalcium phosphate suspension, in which 90% of the brushite particles are smaller than 260 microns and 90% of the brushite particles are larger then 10 microns, using a basic solution of an alkaline earth carbonate for a sufficient period of time to allow the transformation of the brushite calcium phosphate into hydroxyapatite calcium phosphate. Hydrolysis is preferably done by heating an aqueous suspension of brushite.

In one embodiment of the method of the invention, the aqueous solution is heated to the reaction temperature selected, then the carbonate base is introduced. Preferably, calcium carbonate is used as the carbonate base. In this embodiment of the invention, the alkaline hydrolysis of the brushite into calcium phosphate hydroxyapatite can be represented by the following equation:

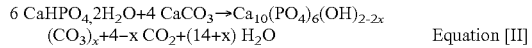
Equation [II]

in which x is between 0 and 1. Preferably, x is between 0.1 and 0.5.

In another embodiment of the method of the invention, the alkaline hydrolysis of the brushite into hydroxyapatite is performed with an alkaline earth carbonate other than calcium carbonate, as represented by the following equation:

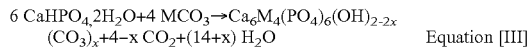
Equation [III]

in which M represents an alkaline earth cation other than calcium, preferably magnesium, and x is between 0 and 1. Preferably, x is between 0.1 and 0.5.

As can be seen from Equations II and III above, according to the method of the invention, the secondary products are carbon dioxide and water, which are easily disposed of.

The granules obtained by the methods described above have physicochemical characteristics described below. The definitions and the methods for determining the characteristics given below are specified in the examples set forth herein.

The calcium phosphate hydroxyapatite granules are white and have a particle size in the range of 1 to 500 microns. Preferably, at least 90% of the particles are larger than 10 microns and 90% of the particles are smaller than 260 microns. The particle sizes can be determined by screening on metal screens. Generally, the size of the particles expressed by the median diameter ($d_{50}$) is between 100 µm and 250 µm, and preferably between 150 µm and 190 µm. The median diameter is defined as being such that 50% by weight of the particles have a larger or smaller diameter than the median diameter.

The hydroxyapatite calcium phosphate granules have a density that is relatively high. The apparent density (non-compressed) of the granules is preferably at least 0.6 and is more preferably still between 0.6 and 1.0, preferably between 0.68 and 0.72. The apparent density (compressed) of the granules is preferably at least 0.7 and is more preferably still between 0.7 and 1.1, preferably between 0.76 and 0.82.

The calcium phosphate granules of the invention have a cohesion suited to satisfactory flow properties for the applications envisioned. The instantaneous flow index is greater than about 7.

The hydroxyapatite calcium phosphate granules have superior compressibility characteristics in comparison with other calcium phosphates. The compressibility profile can be defined as follows:

from 15 to 40 KPa for compression of 30 KN,
from 7 to 25 KPa for compression of 20 KN,
from 3 to 10 KPa for compression of 10 KN.

The calcium phosphate hydroxyapatite granules have a physical shape allowing them to resist attrition, retain significant internal porosity and, as a result, and dissolve at a satisfactory rate when used. The disintegration speed in water of the granules of the invention is less than 60 seconds preferably less than 25 seconds and more preferably still between 5 and 20 seconds.

The hydroxyapatite calcium phosphate in granular form made as described herein results in numerous advantages when these granules are used as excipients. The granules have a much higher direct compression compacting capacity, which, in turn, supplies harder, less friable tablets and reduces the use of binders, thereby reducing costs, the size of the tablets and the energy required to obtain a desired tablet hardness. Furthermore, the granules allow the use of active ingredients that are not particularly compatible with brushite and monetite. Due to improved flow, the granules lead to better uniformity of composition of the tablets obtained, allowing much higher compression speeds and allowing the use of drugs or active ingredients with mediocre flow properties.

While other methods for preparation of hydroxyapatite through the hydrolysis of calcium hydrogenophosphates have been described previously, as in for example U.S. Pat. No. 4,335,086, the present inventors unexpectedly discovered that, by selecting and controlling the particle size of the initial brushite calcium phosphate, the hydroxyapatite granules formed through alkaline hydrolysis with calcium carbonate possess compression properties that are superior both to the initial brushite calcium phosphate and to hydroxyapatite materials produced using different methods.

The hydroxyapatite calcium phosphate can be prepared using a brushite calcium phosphate made using any method known to those skilled in the art that prepares brushite calcium phosphate in the manner described herein. For a hydroxyapatite calcium phosphate to have good flow properties, the hydroxyapatite should preferably have a particle size distribution such that 90% of the particles are smaller than around 260 microns and at least 90% of the particles are larger than around 10 microns. To prepare a hydroxyapatite with this characteristic, the initial brushite calcium phosphate should have a particle size distribution such that 90% of the brushite particles are smaller than around 260 microns and at least 90% of the brushite particles are larger than around 10 microns. This particle size distribution for the brushite may be obtained by eliminating particles outside this range, such as for example by a screening process.

In a preferred embodiment, the size of the starting brushite particles, expressed by the median diameter ($d_{50}$), is between 100 μm and 250 μm and more preferably between 150 μm and 190 μm.

By starting with a brushite calcium phosphate with a particle size distribution that has good flow properties, the method is more effective and more economical in that the quantity of base consumed is used only to hydrolyze the granulometric fraction that is useful in the final hydroxyapatite calcium phosphate. Furthermore, because the final hydroxyapatite product must conform to the regulations governing the use of pharmaceutical components, the brushite calcium phosphate should meet the purity requirements related to pharmaceutical components as they are specified, except in the applicable regulations or standards. For example, the European pharmaceutical specifications for brushite calcium phosphate for use in the pharmaceutical field state that the $CaHPO_4,2H_2O$ content is between 98.0 and 105.5%, the chloride ion content is less than or equal to 330 ppm; the fluoride ion content is less than or equal to 100 ppm; the arsenic content is less than or equal to 10 ppm; the heavy metals and iron contents are respectively less than or equal to 40 ppm and 400 ppm.

In accordance with the method of the invention, an alkaline earth carbonate base is used to produce the hydrolysis reaction. "Alkaline earth" refers to the metals chosen from the group of elements of column 2A of the Periodic Classification of elements and their mixtures, preferably alkaline earths like beryllium, magnesium, calcium, strontium and barium. The bases preferably used completely suited for the method of the invention are calcium carbonate and magnesium carbonate, or mixtures thereof. Most preferably, the base is calcium carbonate. The bases used may be in solid form or in the form of an aqueous suspension having a concentration of between 20% and 40% by weight.

The quantity of carbonate base used is in the approximate range of that defined by the stoichiometry of equation [II] or [III] above. Thus, the base may be provided in a quantity such that it represents about 80 to 110% of the stoichiometric quantity expressed with respect to the brushite calcium phosphate.

The pH of the reaction according to the method of the invention is greater than or equal to 6.0, but it may be higher and vary, for example, between 6.0 and 8.0. It is advantageous to perform the reaction at a temperature higher than ambient temperature. Preferably, the reaction temperature is greater than about 50° C., and more preferably between 60° C. and 100° C. Most preferably, the reaction temperature is around 90° C. At temperatures lower than 50° C., the reaction takes longer and the hydroxyapatite granules obtained may have compressibility properties that are slightly inferior to those of hydroxyapatite granules produced from reactions produced under otherwise identical conditions but at higher temperatures.

The hydrolysis reaction can be produced using any concentration of brushite in aqueous suspension. Preferably, the brushite is stirred sufficiently to keep the brushite in suspension during hydrolysis to provide homogeneous granules of the product. Excessive stirring does not improve the reaction speed and may lead to a fractionation of the particles with a corresponding loss in useful yield. In practice, it is difficult to keep the brushite in suspension when the concentration is greater than around 50% by weight. Preferably, the brushite concentration in the suspension is between about 30 and 40% by weight.

It is preferable to add all of the base at the start of the reaction, but it is possible to add the base progressively as the reaction proceeds. Generally after adding the base, the reactive medium is stirred continuously at the selected temperature for a period of between about 4 and 24 hours, for example.

The process results in the transformation of the brushite calcium phosphate into hydroxyapatite calcium phosphate in which a portion of the anions of the network are replaced by carbonate anions. The quantity of $CO_3^=$ anions represents between about 0.1% and about 10% of the weight of the final carbonated hydroxyapatite, and preferably between about 3 and 6% by weight.

At the end of the reaction, the product is recovered, for example, by filtration or centrifugation. The solid is washed with water and is then dried. Washing may be performed with water used in a proportion so that it generally represents about two times the volume of the solid cake. Drying may be by air drying, preferably by heating the hydroxyapatite calcium phosphate to a temperature of between 80 and 120°, and more preferably around 110° C., to physically eliminate the moisture absorbed. The invention is not limited in this regard, and the hydroxyapatite product may be recovered, washed and dried using any techniques known to those skilled in the art.

The hydroxyapatite calcium phosphate prepared using the method of the invention has an X-ray diffraction pattern typical of the X-ray diffraction pattern of hydroxyapatite. The hydroxyapatite phosphate granules obtained according to this invention may be used in the pharmaceutical field, and may be used in the same applications as calcium phosphate and calcium carbonate. Furthermore, the hydroxyapatite granules have the advantage of providing additional calcium and phosphorous when used in, for example, dietary supplements. Where magnesium carbonate is used as the base in the reaction, the granules may also provide additional magnesium to one's nutritional intake. These elements play an important role in the constitution and functioning of the nerves, the bones, the muscles and teeth.

The granules of the invention have the particular advantage of being directly usable in formulation with active ingredients via direct compression. "Active ingredient" means any product intended for oral use which has a beneficial or desired effect on the user. Thus, the active ingredient may be any product having pharmacological properties, that is, having a preventive or curative effect on a living organism. Also, the active ingredient may be the type provided in parapharmaceutical products such as vitamins or mineral supplements likely to be in tablet form.

Examples of therapeutic active ingredients include anti-rheumetics and nonsteroidal anti-inflammatories (ketoprofen, ibuprofen, flurbiprofen, indometacin, pheylbutazone, allopurinol, nabumetone, etc.), opiate or nonopiate analgesics (paracetamol, phenacetine, aspirin, etc.) cough syrups (codeine, codethyline, alimemazine, etc.), psychotropics (trimipramine, amineptine, chloropromazine and derivatives of phenothiazines, diazepam, lorazepam, nitrazepam, meprobamate, zopiclone and derivatives of the family of cyclopyrrolones, etc,), steroids (hydrocortisone, cortisone, progesterone, testosterone, prednisolone, tiramcinolone, dexamethazone, beamethazone, paramethazone, fluocinolone, beclomethazone, etc.), barbiturates (barbital, allobarbital, Phenobarbital, pentobarbital, amobarbital, etc.), antimicrobial agents (pefloxacine, sparfloxacine and derivatives of the class of quinolones, tetracyclines, synergistines, metronidazole, etc,) drugs intended to treat allergies, particularly anti-asthmatics, antispasmodics and antisecretory agents (omeprazole), cerebral vasodilators (qhinacainol, oxprenolol, propranolol, nicergoline, etc.), brain protectors, liver protectors, therapeutic agents for gastro-intestinal problems, contraceptives, oral vaccines, antihypertensives and cardiovascular or cardioprotector agents such as beta blockers and nitrated derivatives. This listing is not intended to be limiting, and any active ingredient intended to be administered in tablet form may be formulated in combination with the hydroxyapatite of the present invention.

The quantity of active ingredient(s) incorporated in the tablets prepared using the method of this invention may vary within wide limits based upon the particular active ingredient, the desired dosage, and other factors. The quantity of active ingredient may be, for example, between 0.001% and 95% by weight of the total composition, the remainder being the tablet matrix, which is comprised mainly of hydroxyapatite. In general, the hydroxyapatite calcium phosphate forms between 10% and 100% by weight of the matrix. Preferably, the hydroxyapatite comprises at least 80% by weight of the matrix, and more preferably at least 90% by weight of the matrix.

The matrix portion may include a lubricating agent, such as for example magnesium stearate. Preferably, the lubricating agent comprises about 0.5% by weight of the matrix. A disintegrating agent may also be added to the matrix with the granules to encourage the subsequent slaking of the tablets. This may be starch, preferably corn starch or croscarmellose sodium, incorporated in the matrix in a quantity of between about 5 and 10% by weight.

The matrix may also be comprised of one or more pharmaceutically acceptable excipients, more particularly diluting agents, cohesion agents, lubricating agents and coloring agents and flavorings such as saccharides, particularly lactose and sucrose, fatty acids such as stearic acid, for example; polyethyleneglycol; other phosphates such as dicalcium phosphate, silica, silicoaluminates, cellulose derivatives, particularly HMPC, Xanthane gum, gelatin and polyvinylpyrrolidone.

The hydroxyapatite granules of the invention are mixed with the active ingredient(s), and with the other excipients of the composition, using any known solid/solid mixing method and dry compressed via direct compression, that is, without the use of water or an organic solvent such as ethanol. The compression operation following the mixture of the excipients and the active ingredient(s) generally takes place under a force that may range from 6 to 10 kN (measurement at the rock compression level) and preferably from 8 to 9 kN. This compression operation is preferably preceded by pre-compression at a force ranging from 0.5 to 2.5 kN.

High compression speeds can be attained using the method of the present invention, without altering the quality of the tablets. It is, in particular, possible to reach speeds greater than 150,000 tablets/hour, without resulting in cleavage of the tablets.

The tablets obtained according to the invention have the advantage of being able to release the active ingredient quickly, but also have good mechanical properties, particularly friability. The friability of the tablets obtained measured using the method referenced by the American Pharmacopoeia USP 26 under No. 1216 is less than 1%. The disintegration time measured using the method referenced by the American Pharmacopoeia USP 26 under the No. 2040 is less than 1 minute.

In order to illustrate the nature of the invention and its use more completely, two examples of embodiments of the invention are provided. Example 3 is a comparative example where the hydroxyapatite calcium phosphate is prepared by direct precipitation followed by preliminary compacting in granular form.

Before providing detailed examples, the methods used to determine the different properties of the products obtained are provided.

Apparent Density, Compacted and Non-Compacted:

Apparent density, compacted and non-compacted, is measured on an apparatus of the type illustrated in FIG. 1. The empty cylinder (2) is weighed. The powder to be measured is placed in the cylinder (2) using the funnel (1), so that the top of the powder layer is level with top of the cylinder gauged at 250 $cm^3$ (level A). The mass of the powder is determined by weighing the full cylinder. The test tube is anchored firmly in the support (3) by using grips (4). The counter (8), which totals the number of impacts delivered to the bottom of the test tube, is reset to zero.

The test tube is subjected to vertical impacts applied to its base using a hammer (5;) activated by a motor (6) via a cam (7). The operation is stopped when the volume obtained is constant (level B). The change in apparent volume is read on the cylinder scale based on the number of impacts applied using a hammer and the change is recorded. An experimental compression curve is obtained.

Apparent volume=f (number of impacts) that are transformed into an apparent density curve=f (number of impacts).

The apparent density is determined according to the equation:

Apparent density=Mass of the powder introduced (g)
Apparent volume ($cm^3$)

Particle Size:

Particle size is measured by laser light diffraction in aqueous suspensions without ultrasound and without dispersing agent, with a Beckman Coulter LS230™ particle size analyzer, using the Mie theory.

Flow Capacity:

The flow capacity in all the examples is measured using a test performed with a Van-Kel™ Flowmeter model (VK10210). The principle of the test consists in causing 200 grams of material to flow through a "B" "7/16" tablet die. We define the time necessary for the flow of 200 g of material. The pourability is expressed in terms of flow rate or in g/s.

EXAMPLES

Example 1

In this example, the granules are prepared using a discontinuous (i.e. batch) process.

In a double shell reactor, the following ingredients are mixed at 25° C. with stirring at 500 rpm (6 inclined blades): 172 g of dicalcium phosphate dehydrate, $CaHPO_4.2H_2O$, such as that sold under the commercial name DITAB by Rhodia, 60 g of calcium carbonate, $CaCO_3$, such as that obtained from PROLABO, NORMAPUR grade, and 460 g of water.

The total volume of the suspension is about 600 ml and the DITAB concentration is 300 g/l. the suspension is heated to 90° C., the rise in temperature takes about 30 minutes. After 24 hours at 90° C., the heating is stopped and the mixture is allowed to cool to room temperature.

The solid product obtained is then separated by filtration, washed with 3 times the volume of water, and dried for one night in the heat chamber at 100° C.

This product has an X-Ray diffraction pattern typical of hydroxyapatite; its carbonate content is 3% by mass.

Example 2

In this example, the granules are prepared using a semi-continuous method.

In a double shell reactor, the following ingredients are mixed at 25° C. with stirring at 500 rpm (6 inclined blades): 172 g of dicalcium phosphate dehydrate, $CaHPO_4.2H_2O$ (DITAB), and 280 g of water. The total volume of the suspension is about 400 ml.

The suspension is heated to 90° C.; the rise in temperature takes about 30 minutes. When heating begins, begin adding calcium carbonate in suspension comprising 60 g of calcium carbonate, $CaCO_3$, from PROLABO, NORMAPUR grade, and 180 g of water. This addition, made using a peristaltic pump, takes place over 4 hours.

After 24 hours at 90° C., the heating is stopped and the mixture is allowed to cool to room temperature. The solid product is then separated by filtration and washed with 3 times the volume of water, then dried for one night in the heat chamber at 100° C.

This product has an X-Ray diffraction pattern that is typical of hydroxyapatite; its carbonate content is 5% by mass.

Comparative Example 3

A hydroxyapatite calcium phosphate is prepared using a standard method that consists of loading a 12% suspension of calcium hydroxide (weight/weight) into a reactor, loading the suspension at a temperature of 60° C. and then adding a 20% $H_3PO_4$ solution to the lime suspension until the pH of the resulting suspension is between 6 and 7. The suspension is filtered on a vacuum filter and dried at a temperature of 110° C. in an oven for 8 hours.

Hydroxyapatite granules are prepared by feeding the dry product thus obtained into a Fitzpatrick Chilsonator™ system equipped with rollers 10 cm wide and 75 cm in diameter. The rollers have a surface covered with sinusoidal grooves and are separated by a 0.05 cm roller gap. The powdery mixture is fed into the Chilsonator compacting device using a conveyor belt; the mixture is compacted when it passes between the rollers. One roller is hydraulically forced against the other with a pressure of 70 kg/square centimeter (gauge pressure). The roll force is around 2,143 kg per linear centimeter. The rollers have a rotation speed of 16 rpm.

The product exits in sheet form that is fractionated using a Fitzmill™ milling device (model DAS06) equipped with rotating knife blades. The product is unloaded from the milling device through a screen that has round openings of 0.125 cm. The compacted and milled product is then fed directly into a vibrating screening unit.

The screens used have a diameter of 120 cm. The first screen is classed at 36 TBC "tensile bolting cloth" (or a mesh size of 541 μm) and the second screen below is classed at 78 TBC (or a mesh size of 231 μm). The feed load is separated into three portions using these vibrating screens. The median fraction of the particles is recovered, that is, all of the particles that pass through the 36 TBC screen, but that cannot pass through the 78 TBC screen. The higher and lower fractions that emerge from the vibrating screens are sent to the feed hopper of the Chilsonator, mixed with the raw feed load for the Chilsonator and are thus recycled.

Characteristics of the Granules

Figure 2:
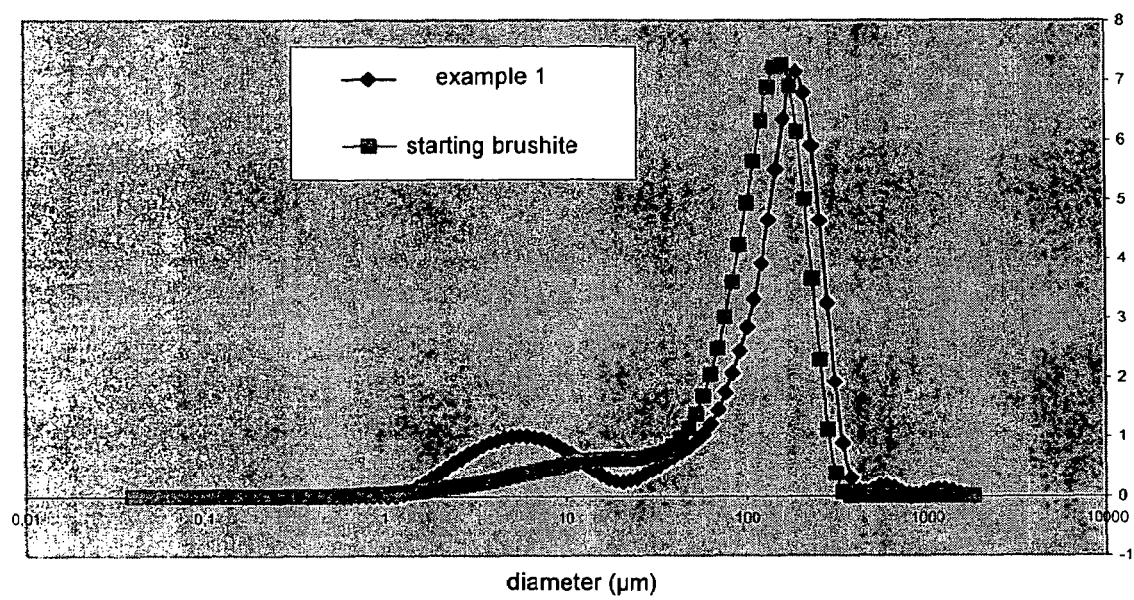
FIG. 2 is a graph showing a comparison of the particle size distribution of the starting brushite material with the calcium phosphate hydroxyapatite produced in Example 1 below.

FIG. 2 is a graph that illustrates the particle size distribution of the granules obtained according to example 1 compared to the particle size of the starting material.

The physicochemical characteristics of the starting material, of the granules obtained according to example 1, as well as the comparative hydroxyapatite phosphate of example 3 are compiled in the Table 1.

TABLE 1

| Material | Apparent density g/cm³ | Flow capacity g/s |
|---|---|---|
| Starting material | 0.870 | 33 |
| Example 1 | 0.72 | 8.1 |
| Comparative example 3 | 0.872 | 16.7 |

Characteristics of Tablets

Tablets are prepared by placing the hydroxyapatite calcium phosphate granules (at a rate of 97 percent) resulting from examples 1 and 3, 2% Ac-Di-Sol™ (croscarmellose stearate) disintegrating agent and 0.5% magnesium stearate lubricating agent in a V-shaped double shell mixer (Patterson Kelley™) equipped with an intensification bar. The mixture is subjected to the mixing process for 2 minutes with the intensification bar in the off position.

The formulations are shaped into tablets by direct compression on a rotating tabletting machine (Manesty™ B3B), equipped with a standard 7/16" IPT cutting tool. The tabletting machine is equipped with tensiometers attached to a recorder in order to record the compression force applied for each lot of tablets. Four of the 16 matrices of the tabletting machine are used.

The tablets are produced at a speed of 750 tablets per minute based on 16 matrices. The nominal weight of the tablets is 675 mg.

The hardness characteristics of the tablets obtained following compression on the machine mentioned above of the starting material, namely brushite calcium phosphate, of the granules of the invention obtained according to example 1, as well as the comparative hydroxyapatite of example 3 are compiled in Table 2 below.

| Compression force (kN) | Hardness of the starting material (kPa) | Hardness of example 1 (kPa) | Hardness of comparative example 3 (kPa) |
|---|---|---|---|
| 10 | 3 | 3 | 1.8 |
| 20 | 7.7 | 7.7 | 4.2 |
| 30 | 15.2 | 15.3 | — |

As will be recognized by those of ordinary skill in the art based on the teachings herein, numerous changes and modifications may be made to the examples and the embodiments described herein without departing from the scope of the invention as defined in the appended claims. Accordingly, this detailed description of preferred embodiments is to be taken in an illustrative, as opposed to a limiting, sense.

The invention claimed is:

1. A method of preparing a calcium phosphate in granular form with an X-ray diffraction pattern characteristic of hydroxyapatite comprising the steps of:
   providing an aqueous suspension of brushite dicalcium phosphate in a reaction vessel wherein the brushite dicalcium phosphate has a particle size distribution such that the median diameter ($d_{50}$) is between 100 μm and 250 μm;
   adding to the brushite dicalcium phosphate suspension a solution of an alkaline earth carbonate base; and
   mixing the suspension for a sufficient amount of time to allow the transformation of the brushite dicalcium phosphate into hydroxyapatite calcium phosphate.

2. The method of claim 1, wherein the carbonate base is selected from the group consisting of calcium carbonate, magnesium carbonate, and mixtures thereof.

3. The method of claim 2, further comprising the step of maintaining the suspension of brushite and carbonate base at a pH of greater than or equal to 6.0.

4. The method of claim 3, further comprising the step of heating the suspension of brushite and carbonate base at a temperature of greater than about 50° C.

5. The method of claim 4, wherein the suspension of brushite and carbonate base is heated to a temperature of about 90° C.

6. The method of claim 4, wherein the quantity of carbonate base used is such that it represents from about 80% to about 110% of the stoichiometric quantity expressed with respect to the brushite calcium phosphate in the suspension.

7. The method of claim 6, further comprising the step of separating the hydroxyapatite calcium phosphate from the aqueous solution by filtration or centrifugation.

8. The method of claim 7, further comprising the step of drying the hydroxyapatite calcium phosphate is at a temperature of between about 80 and about 120° C.

* * * * *